(12) United States Patent
Shochat et al.

(10) Patent No.: US 11,850,032 B2
(45) Date of Patent: *Dec. 26, 2023

(54) METHOD AND SYSTEM FOR MONITORING INTERNAL ELECTRICAL IMPEDANCE OF A BIOLOGICAL OBJECT

(71) Applicant: CARDIOSET LTD, Matan (IL)

(72) Inventors: Michael Shochat, Matan (IL); Schmuel Gummer, Tel Aviv (IL)

(73) Assignee: CARDIOSET LTD., Matan (IL)

( * ) Notice: Subject to any disclaimer, the term of this patent is extended or adjusted under 35 U.S.C. 154(b) by 68 days.

This patent is subject to a terminal disclaimer.

(21) Appl. No.: 17/457,907

(22) Filed: Dec. 6, 2021

(65) Prior Publication Data

US 2022/0233088 A1 Jul. 28, 2022

Related U.S. Application Data

(63) Continuation of application No. 16/872,427, filed on May 12, 2020, now Pat. No. 11,191,442, which is a continuation of application No. 15/539,680, filed as application No. PCT/IL2015/050048 on Jan. 14, 2015, now abandoned.

(51) Int. Cl.
| | | |
|---|---|---|
| *A61B 5/053* | (2021.01) | |
| *A61B 5/0535* | (2021.01) | |
| *A61B 5/276* | (2021.01) | |
| *A61B 5/00* | (2006.01) | |
| *A61B 5/0537* | (2021.01) | |
| *A61B 5/085* | (2006.01) | |

(52) U.S. Cl.
CPC ............ *A61B 5/053* (2013.01); *A61B 5/0535* (2013.01); *A61B 5/276* (2021.01); *A61B 5/0537* (2013.01); *A61B 5/085* (2013.01); *A61B 5/4878* (2013.01); *A61B 5/7221* (2013.01)

(58) Field of Classification Search
None
See application file for complete search history.

(56) References Cited

U.S. PATENT DOCUMENTS

| | | | | |
|---|---|---|---|---|
| 3,750,649 A | | 8/1973 | Severinghaus ...... | A61B 5/0809 600/529 |
| 4,459,993 A | * | 7/1984 | Foreman .............. | A61B 5/0245 600/519 |
| 4,993,423 A | * | 2/1991 | Stice .................... | G01R 17/105 600/509 |
| 5,042,498 A | * | 8/1991 | Dukes .................. | A61B 5/6843 600/509 |

(Continued)

*Primary Examiner* — Benjamin S Melhus
(74) *Attorney, Agent, or Firm* — Reches Patents

(57) ABSTRACT

Method and system for monitoring an internal electrical impedance of a biological object including Internal Thoracic Impedance (ITI) comprising placing two arrays of electrodes on opposite sides of the biological object, wherein each of said two arrays comprise three equally spaced electrodes; imposing an alternating electrical current between pairs of the electrodes and obtaining voltage signals representative of a voltage drop thereon, calculating two values of internal electrical impedance of the biological object corresponding to the uttermost electrodes of said two arrays of electrodes placed on the opposite sides of the biological object.

20 Claims, 5 Drawing Sheets

(56) References Cited

U.S. PATENT DOCUMENTS

| | | | |
|---|---|---|---|
| 5,311,878 A | 5/1994 | Brown | A61B 5/0536 600/547 |
| 5,732,710 A | 3/1998 | Rabinovich | A61B 5/0535 600/536 |
| 5,749,369 A | 5/1998 | Rabinovich | A61B 5/0535 600/372 |
| 5,792,063 A * | 8/1998 | Danielsson | A61B 5/276 600/509 |
| 6,122,544 A | 9/2000 | Organ | A61B 5/0531 600/547 |
| 7,096,061 B2 | 8/2006 | Arad | A61B 5/0536 600/547 |
| 7,158,822 B2 * | 1/2007 | Payne, Jr. | A61B 5/4818 24/306 |
| 9,060,705 B2 | 6/2015 | Holzhacker | A61B 5/6831 |
| 9,271,676 B2 | 3/2016 | Alanen | A61B 5/0531 |
| 9,675,298 B2 | 6/2017 | Kim | A61B 5/7214 |
| 9,974,463 B2 * | 5/2018 | Rutkove | A61B 5/053 |
| 2002/0123674 A1 | 9/2002 | Plicchi | A61B 5/0084 600/300 |
| 2004/0006279 A1 | 1/2004 | Arad (Abboud) | A61B 5/0044 600/506 |
| 2006/0004295 A1 | 1/2006 | Prydekker | |
| 2006/0241513 A1 | 10/2006 | Hatlestad | A61B 5/0809 600/547 |
| 2009/0012381 A1 | 1/2009 | Kuramori et al. | |
| 2010/0106046 A1 | 4/2010 | Shochat et al. | |
| 2013/0172718 A1 | 7/2013 | Choi | A61B 5/6822 600/378 |
| 2014/0046205 A1 | 2/2014 | Arad (Abboud) | A61B 5/0044 600/513 |
| 2014/0148678 A1 | 5/2014 | Drori | |
| 2014/0276166 A1 | 9/2014 | Drori et al. | |
| 2014/0358021 A1 | 12/2014 | Cuba Gyllensten | A61B 5/6823 600/536 |
| 2016/0331266 A1 | 11/2016 | Xiang et al. | |

* cited by examiner

METHOD AND SYSTEM FOR MONITORING INTERNAL ELECTRICAL IMPEDANCE OF A BIOLOGICAL OBJECT

TECHNOLOGICAL FIELD AND BACKGROUND

The present invention relates to noninvasive biological metrology techniques and, more particularly, to a method and device for measuring and/or monitoring an internal electrical impedance of a portion of a biological object, such as the lung(s) or the brain.

Fluid buildup in biological object is associated with many diseases, notably diseases of the heart. An important example of fluid buildup associated with heart disease is acute congestion or edema of the lungs. Because these fluids usually have better electric conductivity than surrounding tissues, changes in liquids volume can be detected by the technique of impedance plethysmography, based on measurements of electrical impedance of whole body or organ of interest.

Clinical signs of pulmonary edema (PED) are appeared on physical examination only after significant lung fluid accumulation and therefore are not sufficiently sensitive to allow clinical monitoring of Heart Failure patients. A decrease in lung impedance (LI) reflects an increase in lung fluid content and may herald evolving PED at very early stage and indicate the need to initiate pre-emptive therapy.

The monitoring of liquid changes within a biological object using two electrodes, one either side of the biological object, is well known in the art. However, this method has proved to be unfit for prolonged monitoring due to the drift of skin-to-electrode contact layer resistance. During prolonged contact between electrode and skin "skin-electrode" impedance is changed as a result of electrolyte penetration to zone of contact and as a result common impedance between two electrodes on both sides of the chest is also changed. In such situation change in common impedance is indicative mainly of variation of "skin-electrode" impedance and not or only in small proportion changes in impedance of internal part of biological object or its portion as for example lung impedance or brain impedance.

A method for overcoming this problem was developed by Kubicek et al. (Annals of the New York Academy of Sciences, 1970, 170(2):724-32; U.S. Pat. No. 3,340,867, reissued as Re. 30,101). Related U.S. patents include Asrican (U.S. Pat. No. 3,874,368), Smith (U.S. Pat. No. 3,971,365), Matsuo (U.S. Pat. No. 4,116,231) and Itoh (U.S. Pat. No. 4,269,195). The method of Kubicek et al. uses a tetra-polar electrode system whereby the outer electrodes establish a current field through the chest. The inner voltage pickup electrodes are placed as accurately as is clinically possible at the base of the neck and at the level of the diaphragm. This method regards the entire portion of the chest between the electrodes as a solid cylinder with uniform parallel current fields passing through it. However, because this system measures the impedance of the entire chest, and because a large part of the electrical field is concentrated in the surface tissues and aorta, this method is not sufficiently specific for measuring variation of liquid levels in the lungs and has low sensitivity: 50 ml per Kg of body weight (Y. R. Berman, W. L. Schutz, Archives of Surgery, 1971. V. 102: 61-64). It should be noted that such sensitivity has proved to be insufficient for obtaining a significant difference between impedance values in patients without pulmonary edema to those with an edema of average severity (A. Fein et al., Circulation, 1979, 60 (5):1156-60). In their report on the conference in 1979 concerning measuring the change in the amount of liquid in the lungs (Critical Care Medicine, 1980, 8(12):752-9), N. C. Staub and J. C. Hogg summarize the discussion on the reports concerning the reports on the method of Kubicek et al. for measuring thoracic bio-impedance. They conclude that the boundaries of the normal values are too wide, and the sensitivity of the method is lower than the possibilities of clinical observation and radiological analysis, even when the edema is considered to be severe. It is indicative that, in a paper six years later by N. C. Staub (Chest. 1986, 90 (4):588-94), this method is not mentioned at all.

Another method for measuring liquid volume in the lungs is the focusing electrode bridge method of Severinghaus (U.S. Pat. No. 3,750,649). This method uses two electrodes located either side of the thorax, on the left and right axillary regions. Severinghaus believed that part of the electrical field was concentrated in surface tissues around the thorax and therefore designed special electrodes to focus the field through the thorax. This method does not solve the problems associated with the drift in the skin-to-electrode resistance described above. An additional problem is the cumbersome nature of the large electrodes required. A review by M. Miniati et al. (Critical Care Medicine, 1987, 15 (12):1146-54) characterizes both the method of Kubicek et al. and the method of Severinghaus as "insufficiently sensitive, accurate, and reproducible to be used successfully in the clinical setting" (p. 1146).

Other notable recent work in measuring the impedance of a portion of the body includes the tomographic methods and apparatuses of Bai et al. (U.S. Pat. No. 4,486,835) and Zadehkoochak et al. (U.S. Pat. No. 5,465,730). In the form described, however, tomographic methods are based on relatively instantaneous measurements, and therefore are not affected by electrode drift. If tomographic methods were to be used for long-term monitoring of pulmonary edema, they would be as subject to problems of skin-to-electrode impedance drift as the other prior art methods.

FIG. 1 schematically illustrates components of Transthoracic Impedance (TTI) with depiction of the thoracic cross-section. Measurement electrodes 3 and 3' are placed on opposite sides of the thorax of a patient. Transthoracic impedance (TTI) 2 generally composed by three components: Internal Thoracic Impedance (ITI) 1 that nearly equals inherent lung impedance (LI) plus high skin-electrode impedances at the front 3 and at the back of the chest 3'. Internal Thoracic Impedance of patients without congestion (normal state) is relatively low 25-120Ω (mean 60Ω) that could be decreased by 15-50% with the development of pulmonary congestion or edema. The skin-electrode impedance is relatively high (200-800Ω) and its value could change as a result of slow variations in skin ionic balance throughout monitoring of several hours' duration. It is also depended from individual characteristics of patients such as skin consistent, weight, height and sex. The absolute values of TTI are typically between 450-1700Ω. The magnitude of ITI decreasing during pulmonary congestion or edema development is approximately 15-50% from normal baseline level (25-120Ω). It means that ITI decreases by 4-60Ω during pulmonary congestion or edema development. Obviously, this change in ITI represents only a small part (1-4%) of the high TTI and is, therefore, barely measurable.

In order to improve sensitivity of ITI measurements was proposed a technique which enables to calculate skin-electrode impedance and it's variations during measurements. Subtracting calculated skin-electrode impedance value from transthoracic impedance TTI provides a solution for a problem of skin-electrode impedance drift and significantly improves sensitivity of ITI measurement.

Such technique disclosed in Rabinovich et al in U.S. Pat. No. 5,749,369 using multi-electrode system for impedance plethysmography with relative immunity to skin-electrode contact resistance drift. The technique uses multiple electrodes defining one measurement and six (plurality) reference electrical circuits. Electrical impedances of all circuits are measured and internal impedance of the biological object is calculated therefrom based on some physical assumptions.

The Edema Guard Monitor (EGM) model RS-207 (RS Medical Monitoring, Israel) was developed according to the U.S. Pat. No. 5,749,369 to address the skin-electrode contact resistance drift monitoring problems. It is designed to non-invasively monitor with better signal-to-noise characteristics than other noninvasive devices.

This system solved the problems of high skin-to-electrode impedances and their drifts during prolonged monitoring by separating ITI from TTI by reducing skin-electrode impedance at the time of each ITI measurement.

The calculated ITI values based on noninvasive measurements thereby correspond to ITI's measurements as if they were performed invasively via electrodes placed within the thorax.

It also known that appropriate location of EGM's electrodes could provide passing electric-magnetic signal outside large arteries and mainly through the lungs' area (as illustrated in FIG. 1). However, lung also contains various heterogeneous structures such a middle size arteries, veins or bronchi and also could contain pulmonary bullae, pulmonary cysts, etc. Such structures usually have different conductivity from surrounding lung tissue.

According to the known noninvasive plethysmography approaches, including EGM's approach, measured values of internal thoracic impedance (ITI) could be affected by the above-mentioned non-uniformities and will not be accurate enough to be sensitive to small ITI (LI) variations.

There is accordingly a need in the art for a novel approach for noninvasive technique solving the problem of limited accuracy/sensitivity to detect small ITI changes occurring during the early stage of interstitial Edema when preventive treatment is desirable and most effective.

GENERAL DESCRIPTION

Thus, according to one broad aspect of the invention, there is provided a method for monitoring an internal electrical impedance of a biological object, comprising placing two arrays of electrodes on opposite sides of the biological object, wherein each of said two arrays comprise three equally spaced electrodes; imposing an alternating electrical current between pairs of said electrodes and obtaining voltage signals representative of a voltage drop thereon, and calculating two values of internal electrical impedance of the biological object corresponding to the uttermost electrodes of said two arrays of electrodes placed on the opposite sides of the biological object.

More specifically, the present invention is useful for monitoring Internal Thoracic Impedance (ITI).

In some embodiments calculated values of internal electrical impedance could be compared therebetween and further could be denied or an accepted based on the comparison result.

Preferably alternating electrical current with frequency from 50 to 200 KHz and having a value from 0.5 to 5 mA could be used. More specifically value from 1 to 2 mA is useful for measurements of Internal Thoracic Impedance (ITI).

According to yet another broad aspect of the invention, there is provided a system for monitoring an internal electrical impedance of a biological object, comprising a plurality of electrodes, current source and a voltage measurement unit connected to an analog multiplexer operable for alternately connecting said current source and said voltage measurement unit to form predetermined sets of said electrodes, a control unit with data processing utility for carrying out calculations and comparing of calculated values of internal impedance.

In some embodiments system for monitoring internal electrical impedance comprises six electrodes and a number of predetermined sets of the electrodes is defined by number of combinations by pairs of the electrodes.

More specifically, the present invention is useful as a medical monitoring system that comprising an impedance plethysmography device, with a plurality of electrodes, current source and a voltage measurement unit connected to an analog multiplexer operable for alternately connecting said current source and the voltage measurement unit to form predetermined sets of said electrodes, a control unit with data processing utility for carrying out calculations and comparing of calculated values of internal impedance. More specifically, current source of the system provides alternating electrical current from 0.5 to 5 mA with a frequency from 50 to 200 KHz.

Plurality of electrodes preferably includes six electrodes and a number of predetermined sets of the electrodes is defined by number of combinations by pairs of the electrodes.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
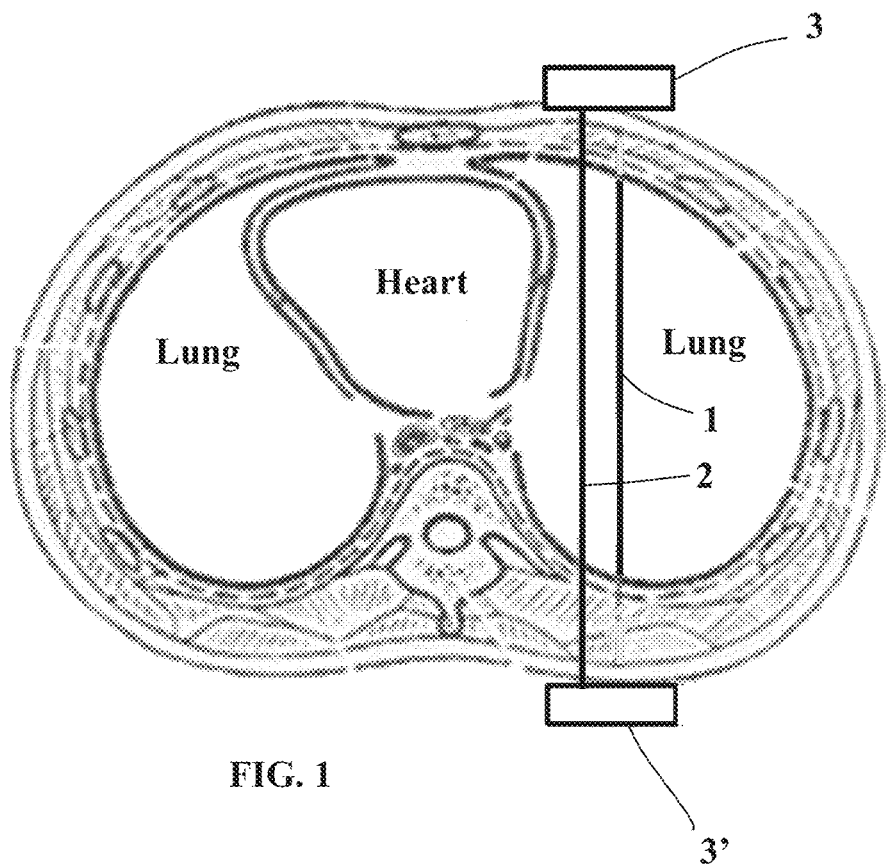
FIG. 1 illustrates components of Transthoracic Impedance (TTI) with depiction of the thoracic cross-section.
Figure 2:
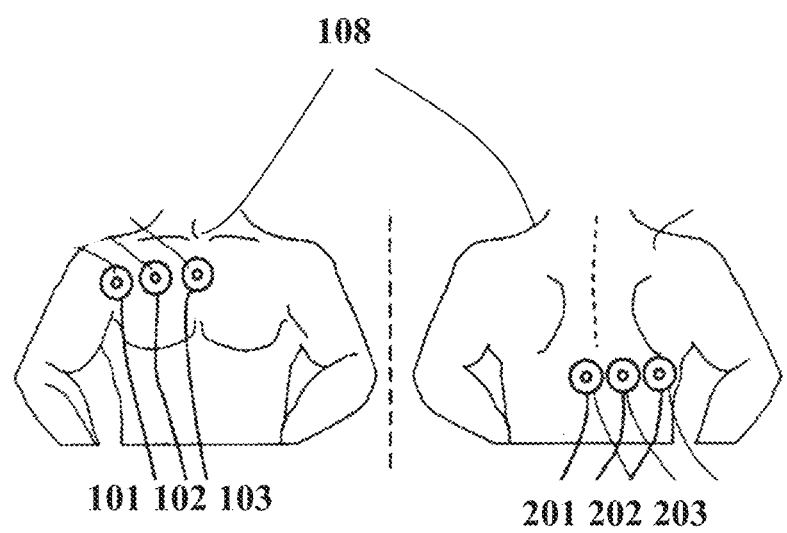
FIG. 2 is a schematic illustration of two arrays of electrodes of impedance plethysmography device used to monitor pulmonary edema.
Figure 3:
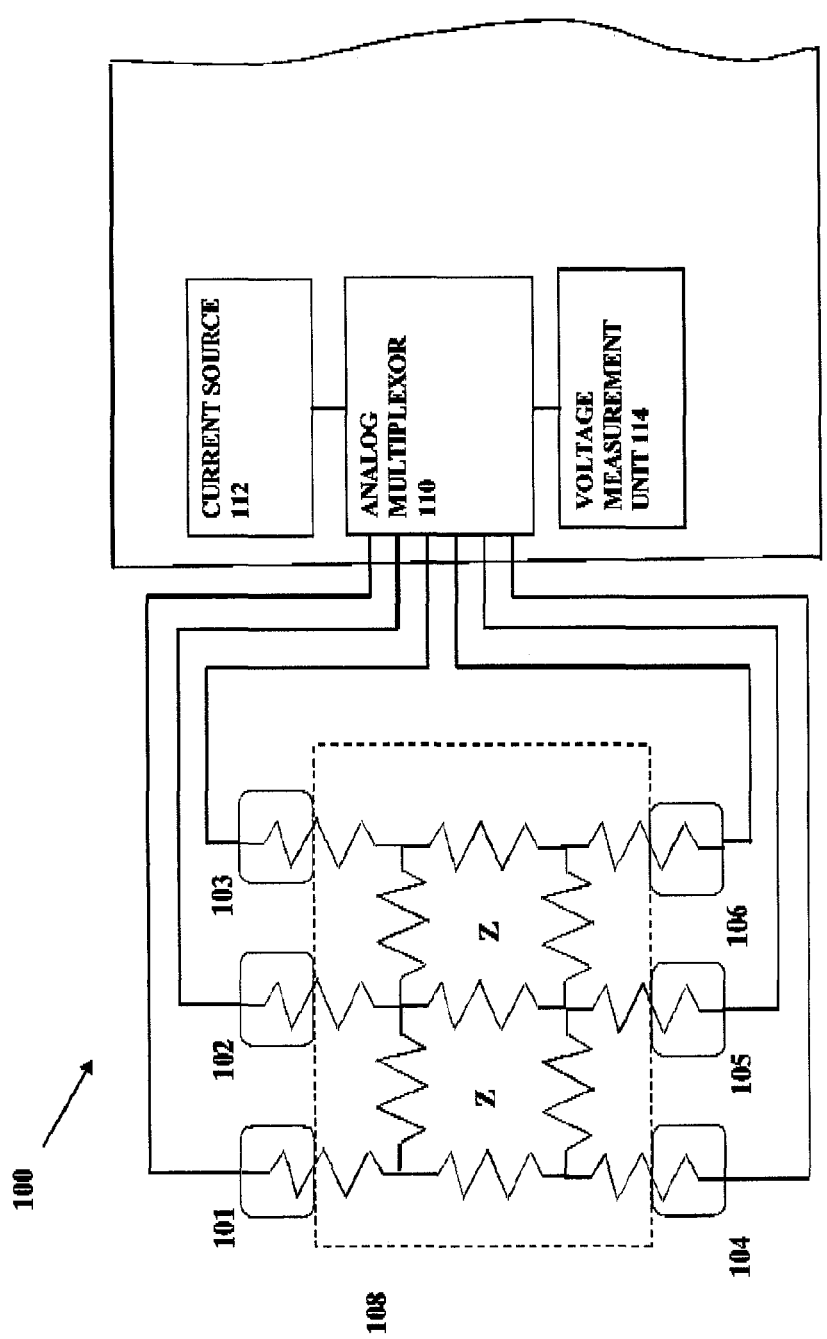
FIG. 3 is a partial schematic illustration of device according to one preferred embodiment FIG. 4A-4B schematically illustrates electric circuitry composed by plethysmography device electrodes and biological object (skin/lung) according to one preferred embodiment of the present invention.

Reference is made to FIGS. 2 and 3 exemplifying the main principles of the invention.

As shown in FIGS. 2 and 3 two arrays of electrodes 101-103 and 104-106 of a system 100 for measuring internal electrical impedance are placed on opposite sides of biological object 108. An analog multiplexer 110 controlled by control unit CU performs selective connecting electrodes 101-106 to a current source 112 and a voltage measurement unit 114. Selective connecting of electrodes 101-106 could form pre-determined sets of electrodes comprising desired number of electrodes of any one or both arrays of electrodes.

Sets formed by electrodes placed on the same side of biological object 108 i.e. 101-103 or 104-106 forms "reference" circuits and sets formed by at least two electrodes of different group's forms measurement circuits. It should be noted that pre-determined sets of electrodes comprise at least two electrodes. Analog multiplexer 110 is capable to connect any desired combinations of electrodes 101-106 forming pre-determined sets.

Preferably each array comprises three equally spaced electrodes and are placed on opposite sides of the biological object, e.g. opposite sides of the thorax of a patient in case of impedance plethysmography (as illustrated specifically in FIG. 2).

Current source 112 supplies alternative electrical current of substantially identical intensity, e.g. of about 0.5-5 mA between electrodes of any predetermined set.

For impedance plethysmography preferably, current from about 1 mA to about 2 mA at a frequency of between about 50 KHz and about 200 KHz is used. Current of about 1 mA most preferably could be used. The term "frequency", as used herein, refers to the fundamental frequency of a periodic waveform, so that the scope of the present invention includes alternating current of any periodic waveform, for example square, saw, etc. waves, and not just sinusoidal alternating current.

A voltage drop V across the measurement and reference circuits is measured by voltage measurement unit 114 while imposing an alternative current between circuit's electrodes. Generally, voltage drop across the measurement circuits being indicative of (proportional) a total impedance of the biological object and voltage drop across the reference circuits being indicative of (proportional) skin-electrode impedance.

The inventors have found that for improving impedance plethysmography all possible sets each including only pair of electrodes (forming both measurement and reference circuits) could be used. In that case, number of sets (pairs) is defined by number of combinations by pairs of electrodes.

It is to be understood that the preferred embodiment of FIG. 3 is illustrative. In particular, the scope of the present invention is not restricted to circuitry in which voltage drops across the measurement circuit and the reference circuits are measured explicitly, but rather includes all circuitry which accomplished the ends of the method of the present invention, using signals representative of the voltage drops across measurement circuit and the reference circuits respectively.

Figure 4B:
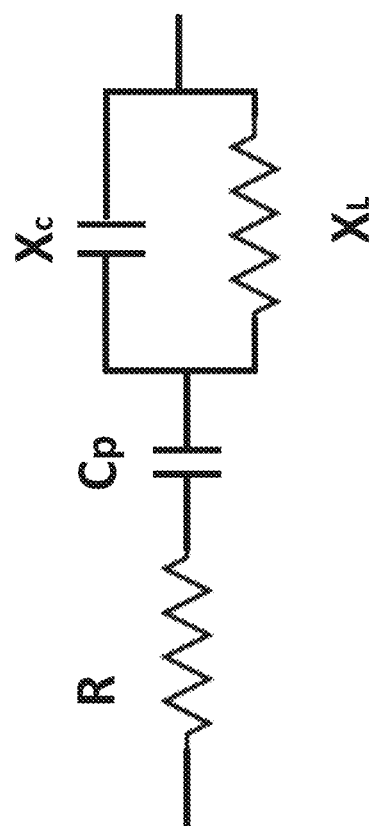
Figure 4A:
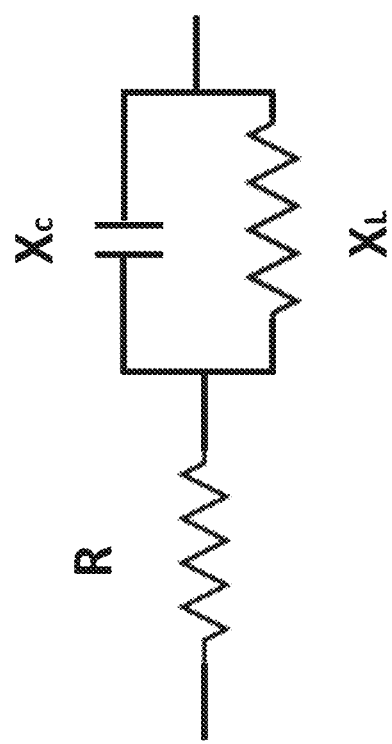

Referring to FIG. 4A-4B preferably not all measurement circuits could be used directly for characterizing Internal Thoracic Impedance (ITI) as will be explained further below. For example, calculated internal impedances corresponding only to the measurement circuits formed by pairs of uttermost electrodes of opposite arrays (101, 106) and (103,104) could be used. Values of seven internal impedances corresponding to the rest measurement circuits including pairs of electrodes of opposite arrays are not calculated. However, impedance of these measurement circuits are used for calculating values of Internal Thoracic Impedance (ITI) based on some physical assumptions as will be explained further below.

Using of plurality of measured impedances corresponding to measurement circuits performing measurements on different areas of lung could improve accuracy of measurements due to decreasing effect of possible local non-uniformities or anomalies such as bullae within the lungs. Hence, during ITI monitoring (for a long period) the measurements could be performed periodically with replacement of measuring electrodes. Some deviation in location of measuring electrodes could occur and in such cases local non-uniformities or anomalies such as bullae could cause sufficient variations of measurement results. Using a plurality of electrodes covering different areas of lung (with different current ways) and "averaging" obtained ITI measured results could reduce such negative effect caused by local non-uniformities or anomalies. In addition, multiple measurements used for calculating internal impedance(s) also could improve accuracy of obtained result.

Turning back to FIG. 4A-4B the configuration and operation of the system 10 of the invention is now more specifically exemplified, effective electric circuit (circuitry) composed by plethysmography device electrodes and biological object (skin/lung). Effective electric circuit is based on physical assumption that the total impedance measured across two electrodes placed on opposite sides of the biological object is the sum of two impedances: the impedance of the skin-electrode contacts and the internal impedance of the body.

Generally the impedance $Z_M$ of any measurement circuit formed by set of electrodes is the sum of the following impedances:

$$Z_M = Z_{IN} + Z_A + Z_B \quad (A)$$

Where:
$Z_{IN}$—the internal impedance of biological object (e.g. ITI);
$Z_A$—"transition" impedance which includes the impedance of first electrode; the impedance of the skin-electrode contact of electrode; and skin impedance;
$Z_B$—"transition" impedance which includes the impedance of second electrode; the impedance of the skin-electrode contact of electrode; and skin impedance.

On the other hand, the impedance of any reference circuit formed by set of electrodes is representative of "transition" impedances only, i.e. the sum of the following impedances:

$$Z_R = Z_A + Z_B \quad (B),$$

Where:
$Z_A$—"transition" impedance which includes the impedance of first electrode; the impedance of the skin-electrode contact of electrode; and skin impedance;
$Z_B$—"transition" impedance which includes the impedance of second electrode; the impedance of the skin-electrode contact of electrode; and skin impedance Thus, internal impedance of biological object (e.g. ITI in our case) $Z_{IN}$ could be calculated using voltage drops across measurement and reference circuits based on effective electric circuitry illustrated in FIG. 4A-4B At least two measurement circuits formed by sets comprising electrodes with substantially equal (similar) distance therebetween are used according to the present invention.

Measurement and reference circuits of the present invention could be characterized by the following impedances:
$Z_1$—impedance of electrode and skin-electrode contact of electrode 101;
$Z_2$—impedance of electrode and skin-electrode contact of electrode 102;
$Z_3$—impedance of electrode and skin-electrode contact of electrode 103;
$Z_{11}$—impedance of electrode and skin-electrode contact of electrode 104;

$Z_{12}$—impedance of electrode and skin-electrode contact of electrode 105;

$Z_{13}$—impedance of electrode and skin-electrode contact of electrode 106;

$Z_4$—skin impedance between electrode 101 and 102;

$Z_5$—skin impedance between electrode 102 and 103;

$Z_9$—skin impedance between electrode 104 and 105;

And $Z_{10}$—skin impedance between electrode 105 and 106.

Sets of electrodes forming measurement circuits could comprise from minimum two up to all electrodes of both groups of electrodes while sets of electrodes forming reference circuits could comprise from minimum two and up to all electrodes of one of the groups of electrodes.

In order to be able calculate plurality (at least two) internal impedances of biological object (e.g. ITI) appropriate number of measurements by should be performed.

Figure 5:
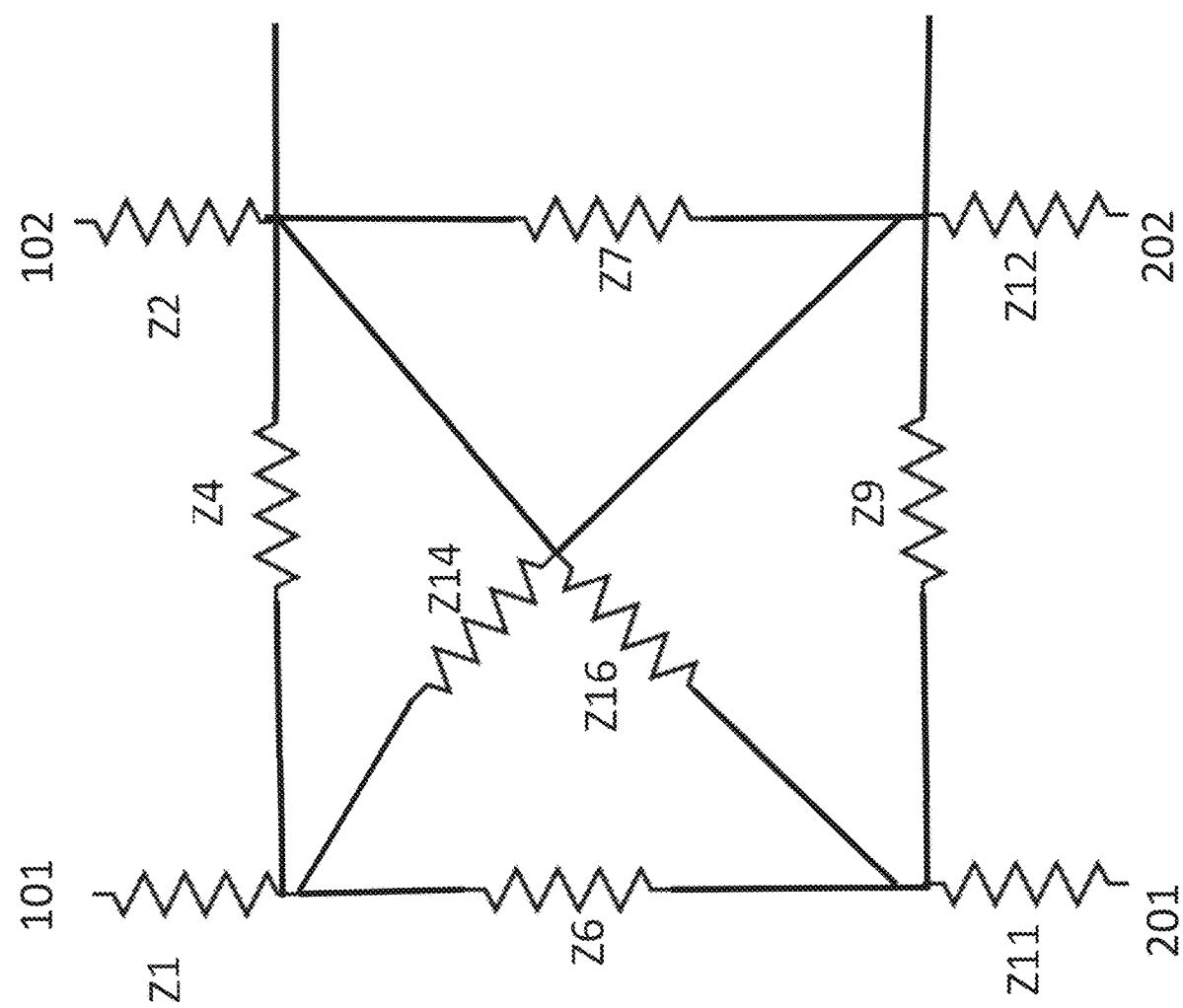
FIG. 5 schematically illustrates electric circuitry composed by plethysmography device electrodes and biological object (skin/lung) according to another preferred embodiment of the present invention.

Reference is made to FIG. 5 exemplifying the effective electric circuit (circuitry) composed by plethysmography device electrodes and biological object (skin/lung) according to preferred embodiment of the present invention. According to this embodiment each set of electrodes forming measurement and reference circuits comprise a pair of electrodes and number of sets (pairs) is defined by number of combinations by pairs of all electrodes. For six electrode's scheme, e.g. used in Edema Guard Monitor (EGM) model RS-001 (RS Medical Monitoring, Israel) total number of sets (pairs) is 15 and accordingly 15 measurement sessions providing 15 values of impedance $M_1$-$M_{15}$ are performed. Each of measurement session defines impendences of whether of measurement or reference circuits calculated according to Ohm's Law based on the measured values of voltage drops. According to the present invention, internal impedance $Z_{in}$ of biological object (lung in the present example) could be calculated using the following 15 measured impedances $M_1$-$M_{15}$ of 15 circuits formed by pairs of electrodes:

$$Z_1+Z_6+Z_{11}=M_1$$

$$Z_1+Z_4+Z_2=M_2$$

$$Z_2+Z_5+Z_3=M_3$$

$$Z_1+Z_4+Z_4+Z_3=M_4$$

$$Z_2+Z_7+Z_{12}=M_5$$

$$Z_3+Z_8+Z_{13}=M_6$$

$$Z_{11}+Z_9+Z_{12}=M_7$$

$$Z_{12}+Z_{10}+Z_{13}=M_8$$

$$Z_{11}+Z_9+Z_{10}+Z_{13}=M_9$$

$$Z_1+Z_{14}+Z_{12}=M_{10}$$

$$Z_2+Z_{16}+Z_{11}=M_{11}$$

$$Z_2+Z_{15}+Z_{13}=M_{12}$$

$$Z_3+Z_{12}+Z_{12}=M_{13}$$

$$Z_1+Z_{19}+Z_{13}=M_{14}$$

$$Z_{11}+Z_{18}+Z_3=M_{15}$$

Where in addition to impendences presented in FIG. 3 as described above, two additional impendences $Z_{18}$ and $Z_{19}$ are introduced being internal impedances of biological object (e.g. ITI) corresponding to measurement circuit composed by pairs of "uttermost" opposite electrodes (101,106) and (103,104).

According to the present invention totally 19 values of impedances including impedances of electrodes and skin-electrode contacts and 9 internal impedances of biological object (e.g. ITI) ($Z_6$, $Z_7$, $Z_8$, $Z_{14}$, $Z_{15}$, $Z_{16}$, $Z_{17}$, $Z_{18}$ and $Z_{19}$) could be obtained by solving a system of the above 15 linear equations corresponding to 15 measurement sessions. The following physical assumption should be applied in order to be able to get 19 values from 15 linear equations: $Z_6=Z_7=Z_8$ and $Z_{14}=Z_{15}=Z_{16}=Z_{17}$.

In that case 19 values of impedances could be calculated as following:

$$Z_1=(2M_1+2M_2+2M_3-2M_4-2M_5+M_{10}-M_1):2$$

$$Z_2=(M_2+M_3-M_4):2$$

$$Z_3=(2M_3-M_{10}+2M_1+2M_2+2M_3-2M_4-2M_5-M_{11}):2$$

$$Z_4=(2M_5-2M_1-M_2-3M_3+3M_4-M_{10}+M_{11}):2$$

$$Z_5=(M_{10}-2M_1-3M_2-M_3+3M_4+2M_5+M_{11}-2M_{13}):2$$

$$Z_6=Z_7=Z_8$$

$$Z_7=(2M_5-M_2-M_3+M_4-M_7-M_8+M_9):2$$

$$Z_9=(2M_5-M_{11}+M_{10}-2M_1-M_2-M_3+M_4-2M_8+2M_9):2$$

$$Z_{10}=(2M_5-2M_7+2M_9-2M_{12}+M_{10}-2M_1-M_2-M_3+M_4+M_{11}):2$$

$$Z_{11}=(M_{11}-M_{10}+2M_1+M_2+M_3-M_4-2M_5+M_7+M_8-M_9):2$$

$$Z_{12}=(M_7+M_8-M_9):2$$

$$Z_{13}=(2M_{12}-M_{10}+M_7+M_8-M_9+2M_1+M_2+M_3-M_4-2M_5-M_{11}):2$$

$$Z_{14}=(M_{10}-2M_1-2M_2-2M_3+2M_4+2M_5+M_{11}-M_7-M_9):2$$

$$Z_{14}=Z_{15}=Z_{16}=Z_{17}$$

$$Z_{18}=(2M_{14}-4M_1-3M_2-3M_3+3M_4+4M_5+2M_{11}-2M_{12}-M_7-M_8+M_9):2$$

$$Z_{19}=(2M_{15}+2M_{10}-4M_1-3M_2-3M_3+3M_4+4M_5-M_7-M_8+M_9-2M_{13}):2$$

Performing maximal possible number of measurements for multi-electrode (six—in the present example) system provides most efficient way of system operation.

Preferably, only values of internal impedances $Z_{18}$ and $Z_{19}$ corresponding to measurement circuits defined by "uttermost" opposite electrodes could be calculated and used for characterizing internal impedance of the biological object (e.g. ITI). Since the inter-electrodes space in that case covers maximum biological object (e.g. lung) tissue these measurements could be most representative of variations of liquid amount within the lung tissue.

Combing (e.g. averaging) of calculated values internal impedances $Z_{18}$ and $Z_{19}$ could sufficiently improve accuracy of measurements by further decreasing affecting of possible local non-uniformities or anomalies within the lungs.

The inventors have found that internal impedance of biological object $Z_{18}$ and $Z_{19}$ (lung in the present example) could be calculated based on assumption that ITI corresponding to measurement circuits with similar distance between electrodes have substantially the close values.

To this end, impedances $Z_6$, $Z_7$ and $Z_8$ corresponding to measurement circuits comprising opposite electrodes, such as first outer electrodes 101-104, internal electrodes 102-105 and second outer electrodes 103-106 are considered as having substantially the same values:

$$Z_6 = Z_7 = Z_8$$

Also internal impedances $Z_{14}$, $Z_{15}$, $Z_{16}$ and $Z_{17}$ are considered as having substantially the same values:

$$Z_{14} = Z_{15} = Z_{16} = Z_{17}$$

If lung tissue does not include heterogeneous structures and is homogenous on the pass of electromagnetic signals, internal impedances $Z_6$, $Z_7$, $Z_8$ as well $Z_{14}$, $Z_{15}$, $Z_{16}$, $Z_{17}$ will have substantially equal values. In that case, accuracy of calculated internal impedances $Z_{18}$ and $Z_{19}$ will increase due to performing maximal possible number of measurements.

When lung tissue includes heterogeneous structures within the pass of electromagnetic signal between at least one pair of electrodes, there could be some difference between the values of internal impedances in at least one of the groups $Z_6$, $Z_7$, $Z_8$ and $Z_{14}$, $Z_{15}$, $Z_{16}$ $Z_{17}$. In such case value of internal impedances used for calculating will be effectively "averaged" and effect of heterogeneous structures on calculated impedances $Z_{18}$ and $Z_{19}$ will be decrease.

According to another preferred embodiment, In order to provide even more accurate measurements, calculated values of $Z_{18}$ and $Z_{19}$ could be compared therebetween.

Since the measurements are performed on live non-static biological object, e.g. human patient, various parts of breath cycle, un-controlled movements etc. could cause substantial changes of measurement conditions. Such changes could affect obtained values of internal impedances and decrease accuracy of final calculated result. To this end, pre-set value of difference between $Z_{18}$ and $Z_{19}$ could be used for measurements verification. Such pre-set value typically could be selected not exceeding 3 Ohms.

In case when difference between values of $Z_{18}$ and $Z_{19}$ does not exceeded (is less) pre-set value such measurement session(s) will be accepted and calculated values $Z_{18}$ and $Z_{19}$ could be used for diagnostic purposes.

Additionally, averaging of calculated values $Z_{18}$ and $Z_{19}$ could be performed.

Contrary, in case when difference between values of $Z_{18}$ and $Z_{19}$ does increase pre-set value such measurement session(s) will be rejected or discarded. Further, measurement session(s) could be repeated till acceptable result will be obtained as described above.

Figure 6:
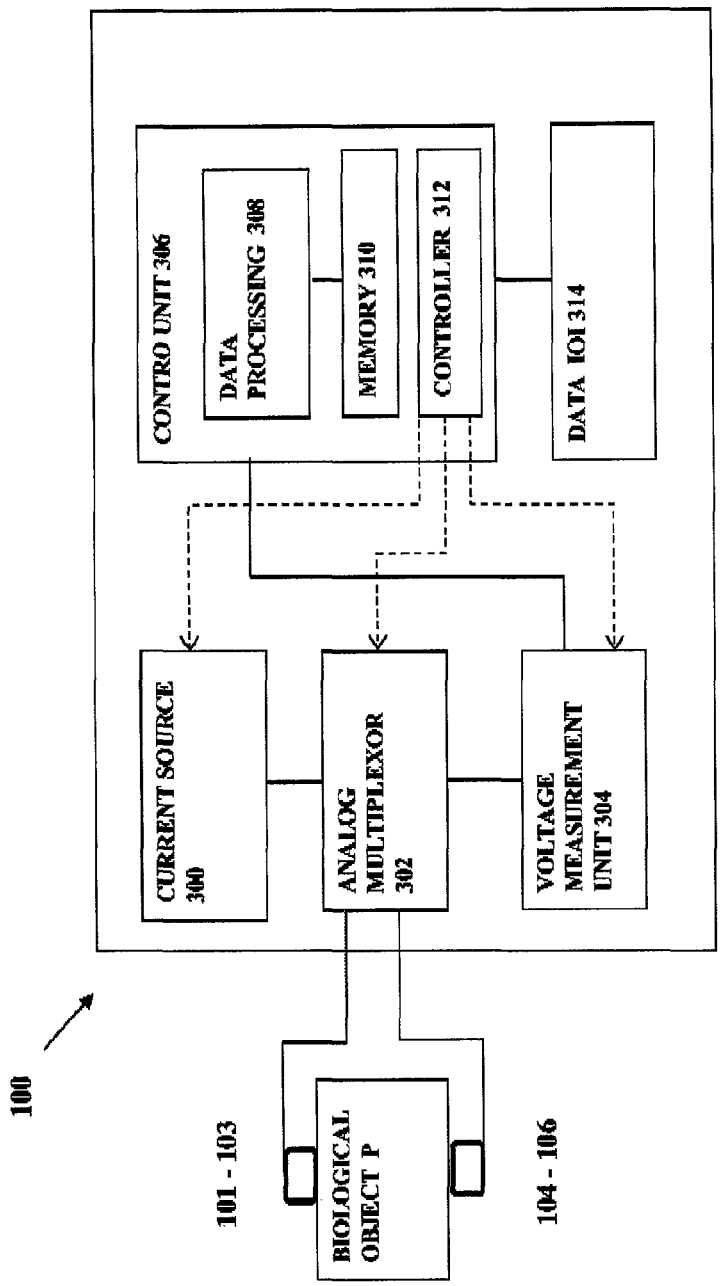
FIG. 6 is a schematic block diagram of the system according to the present invention

Appropriate utility of control unit (e.g. control unit 306 of FIG. 6) could be provided enabling comparing of calculated values of internal impedance of biological object (e.g. ITI) and performing additional measurement sessions. In addition, inputting and storing of the above-mentioned pre-set value could be performed using appropriate Input/Output interface—IOI and data storage unit.

The calculation of the actual impedance values of the skin-electrode contacts of electrodes 101 106 enables to carry out long-term monitoring of the electrical impedance of a biological object with compensation for skin-electrode resistance drifts, even when the impedance values of the skin-electrode contacts are substantially different.

Reference is made to FIG. 5 exemplifying the configuration of system 100 of the present invention specifically useful for impedance plethysmography. As shown in FIG. 5 system 100 according to the present invention preferably includes: current source 300; analog multiplexer 302 for alternately connecting current source 300 to predetermined set of electrodes forming whether measurement or reference electrical circuits; a voltage measurement unit 304; a control unit 306 that includes data processing utility 308 for carrying out calculations; a data-storage unit (memory) 310 for storing data during the measurement sessions and monitoring period; a controller utility 312 for controlling the operation of units of system 100 such as current source 300, analog multiplexer 302, voltage measurement unit 304, etc.; data Input/Output interface—IOI 314. Data IOI 314 could include appropriate buttons, display, touch-screen enabling input of commands, data, etc. for operating the system 100 and displaying operating status of the system and measurement data. An alarm unit also could be provided (not-shown)

Data processing utility 308 could comprise appropriate SW and HW that is connectable to data-storage unit 310, data IOI 315 and optionally to alarm unit. These SW and HW provide operation of system 100 according to the method described above.

System 100 could be powered from external (e.g. AC) and/or internal (e.g. battery) sources by means of a power supply (not shown).

Voltage measurement unit 304 typically includes rectifier (not shown) for obtaining the absolute value of the signals representing the voltage drops and analog to digital A/D converter for converting analog signals to a digital form signal compatible with data processing utility 308.

When using a device according to the present invention, electrical source 300 is alternately connected to each of the electrical circuits formed by pre-determined sets of electrodes 101-106 shown in FIG. 5 by means of analog multiplexer (commutator) 302. Signal representing the voltage drop of a specific electrical circuit is fed voltage measurement unit 304 which preferably provides signal in digital form. The obtained digital signal is fed into control unit 306 for storing in data-storage unit (memory) 310 for further processing by data processing utility 308.

Control unit 306 orders analog multiplexer (commutator) 302 to form pre-determined number and configurations of measurement and reference circuits, e.g. 15 for six-electrodes scheme with two-electrodes sets of electrodes.

After data-storage unit (memory) 310 has received data from each of electrical circuits, data processing utility 308 can calculate the internal impedances $Z_{IN}$ (values of $Z_{18}$ and $Z_{19}$) according to the method described above. Data processing utility 308 also could perform additional processing of multiple measurement results, e.g. comparison of values of $Z_{18}$ and $Z_{19}$ and their combining due to pre-set algorithm (averaging, weighing, etc.).

Preferably, when performing a monitoring of a biological object the process described above is carried out periodically, so that Data processing utility 308 can simultaneously calculate the values of the internal impedance $Z_{IN}$ as well as changes therein. The change in $Z_{IN}$ may be calculated, for example, as the difference between the last value and the initial or previously measured value(s) or as a percentage therefrom. The results of the calculations could be transmitted to data IOI interface 14 and displayed by internal or external display, to data-storage unit (memory) 310, and to optional alarm unit.

In the event that the value of $Z_{IN}$ has decreased below a critical value, and/or in the event that the change in $Z_{IN}$ has exceeded a critical value, the alarm could be activated.

Data-storage unit (memory) 310 may provide data for analysis during the monitoring period so as to monitor the progress of the disease.

Thus, the present invention provides an effective and reliable technique for measuring the internal electrical impedance of a biological object and specifically Transthoracic impedance which can be used for effective monitoring in time of lung liquid volume status.

Those skilled in the art will readily appreciate that various modifications and changes can be applied to the embodiments of the invention hereinbefore described without departing from its scope defined in and by the appended claims.

The invention claimed is:

1. A method for multi-electrode monitoring of an internal electrical impedance of a biological object, the method comprising the steps of:
   i) placing a first array of electrodes on one side of the biological object and a second array of electrodes on an opposite side of the biological object, wherein each of said arrays comprises at least three spaced apart electrodes;
   ii) performing a plurality of measurements on different pairs of electrodes that comprise two or more opposite sides electrode pairs, wherein each of said measurements is performed on a different pair of said electrodes by applying an alternating electrical current between the electrodes of the pair and obtaining voltage signals representative of a voltage drop thereon; wherein each opposite sides electrode pair comprises an electrode of the first array and an electrode of the second array;
   iii) calculating, for each electrode (of the different pairs of electrodes), values of impedance(s) indicative of sums of electrode impedance and a skin-electrode contact impedance to provide multiple values;
      wherein said calculating comprises using a system of linear equations;
   iv) comparing said calculated sums to each other, wherein a difference between sums, found by the comparing, that exceeds a predetermined threshold value is representative of a potential failure in at least one of said electrodes related to the sums;
   v) calculating an internal electrical impedance value of the biological object based on (a) measurements of at least two opposite sides electrode pairs of the two or more opposite sides electrode pairs, and (b) calculated sums for each electrode of the at least two opposite sides electrode pairs; and
   wherein the method comprising performing measurement sessions by repeating steps ii)-v) when the result of the comparison exceeds the predetermined threshold value.

2. The method of claim 1 further comprising defining a correctness of one or more measurements obtained during the measurement sessions or a faultlessness of at least one of the electrodes based on said result of the comparing.

3. The method of claim 2 further comprising denying acceptance of the measurement sessions.

4. The method of claim 2 further comprising replacing any faulty electrode.

5. The method of claim 1 wherein said biological object includes a human body.

6. The method according to claim 1 wherein said predetermined threshold value is 150 Ohm.

7. The method according to claim 1 wherein said internal electrical impedance of the biological object includes an Internal Thoracic Impedance (ITI).

8. The method according to claim 7 wherein said alternating electrical current has a value from 0.5 to 5 mA.

9. The method of claim 8 wherein said alternating electrical current has a value from 1 to 2 mA.

10. The method according to claim 8 wherein said alternating electrical current has a frequency from 50 to 200 KHz.

11. The method of claim 8 wherein said alternating electrical current includes alternating current of any periodic waveform.

12. The method of claim 7 wherein a number of said applying is defined by number of combinations by said pairs of electrodes.

13. The method according to claim 1 wherein the two or more opposite sides electrode pairs comprises any combination between any electrode of the first array and any electrode of the second array.

14. The method according to claim 1 wherein the two or more opposite sides electrode pairs comprises only some of any combination between any electrode of the first array and any electrode of the second array.

15. The method according to claim 1 wherein the calculating of the internal electrical impedance value comprises averaging the measurements of the at least two opposite sides electrode pairs.

16. The method according to claim 1 wherein the calculating of the internal electrical impedance value comprises combining the measurements of the at least two opposite sides electrode pairs by using a pre-set algorithm.

17. The method according to claim 1 wherein biological object is a lung and wherein the calculating of the internal electrical impedance value comprises combining the measurements of the at least two opposite sides electrode pairs by using a pre-set algorithm.

18. The method according to claim 1 wherein a number of the linear equations is smaller than a number of the plurality of measurements.

19. The method according to claim 1 wherein the calculating using the system of linear equations is based on an assumption that internal impedances of equal-length paths within the biological object are equal to each other.

20. A method for multi-electrode monitoring of an internal electrical impedance of a biological object, the method comprising the steps of:
   i) placing a first array of electrodes on one side of the biological object and a second array of electrodes on an opposite side of the biological object, wherein each of said arrays comprises at least three spaced apart electrodes;
   ii) performing a plurality of measurements on different pairs of electrodes that comprise two or more opposite sides electrode pairs, wherein each of said measurements is performed on a different pair of said electrodes by applying an alternating electrical current between the electrodes of the pair and obtaining voltage signals representative of a voltage drop thereon; wherein each opposite sides electrode pair comprises an electrode of the first array and an electrode of the second array;
   iii) calculating, for each electrode (of the different pairs of electrodes), values of impedance(s) indicative of sums of electrode impedance and a skin-electrode contact impedance to provide multiple values; wherein said calculating comprises using a system of linear equations based on an assumption that internal impedances of equal-length paths within the biological object are equal to each other;
   iv) comparing said calculated sums to each other, wherein a difference between sums, found by the comparing, that exceeds a predetermined threshold value is representative of a potential failure in at least one of said electrodes related to the sums; and v) calculating an internal electrical impedance value of the biological object based on (a) measurements of at least two opposite sides electrode pairs of the two or more opposite sides electrode pairs, and (b) calculated sums for each electrode of the at least two opposite sides electrode pairs.

\* \* \* \* \*